United States Patent [19]

Kausek et al.

[11] Patent Number: 4,633,867
[45] Date of Patent: Jan. 6, 1987

[54] KNEE BRACE FOR CONTROL OF LIGAMENT INSTABILITY

[75] Inventors: James H. Kausek, 85 Salem St., Lynnfield, Mass. 01940; Alfred Klugman, Waban; William J. Donovan, Somerville, both of Mass.

[73] Assignee: James H. Kausek, Lynnfield, Mass.

[21] Appl. No.: 624,990

[22] Filed: Jun. 27, 1984

[51] Int. Cl.$^4$ .............................................. A61F 5/00
[52] U.S. Cl. .................................... 128/80 C; 128/88
[58] Field of Search ................... 128/80 C, 80 R, 88, 128/87 R, 165; 2/22, 24

[56] References Cited

U.S. PATENT DOCUMENTS

| | | | |
|---|---|---|---|
| 3,055,359 | 9/1962 | Palmer | 128/88 X |
| 3,785,371 | 1/1974 | Lewis | 128/165 X |
| 4,041,940 | 8/1977 | Frankel et al. | 128/87 R X |
| 4,139,002 | 2/1979 | Almedia | 128/80 C |
| 4,506,661 | 3/1985 | Foster | 128/80 C |

*Primary Examiner*—Mickey Yu
*Attorney, Agent, or Firm*—Wolf, Greenfield & Sacks

[57] ABSTRACT

A knee brace for controlling ligament instability in all planes while allowing full natural action of the knee. The brace includes a shin plate and a thigh plate connected in hinged relationship. The shin plate has a pair of flanges extending from opposing corners of its top edge which are positionable over the side tibia tubricals. A tensioned popliteal strap attached at opposing ends to opposing flanges is positionable in a substantially horizontal plane around the back of the upper calf adjacent the knee to compress the flanges against the side tibia tubricals for increasing the rotational stability of the knee. The interior of the shin plate is parabolic-shaped to prevent chafing against the crest of the tibia and the elongated edges of the shin plate grasp opposing sides of the triangular-shaped tibia to further increase the rotational stability of the knee. An adjustable extension check strap, which prevents a complete unbending of the knee, passes through a ring positioned on the back of a calf band. A condylar pad attached to the brace is positionable to engage the medial femoral epicondyl and condyl notch for preventing displacement of the knee brace on the leg.

9 Claims, 9 Drawing Figures

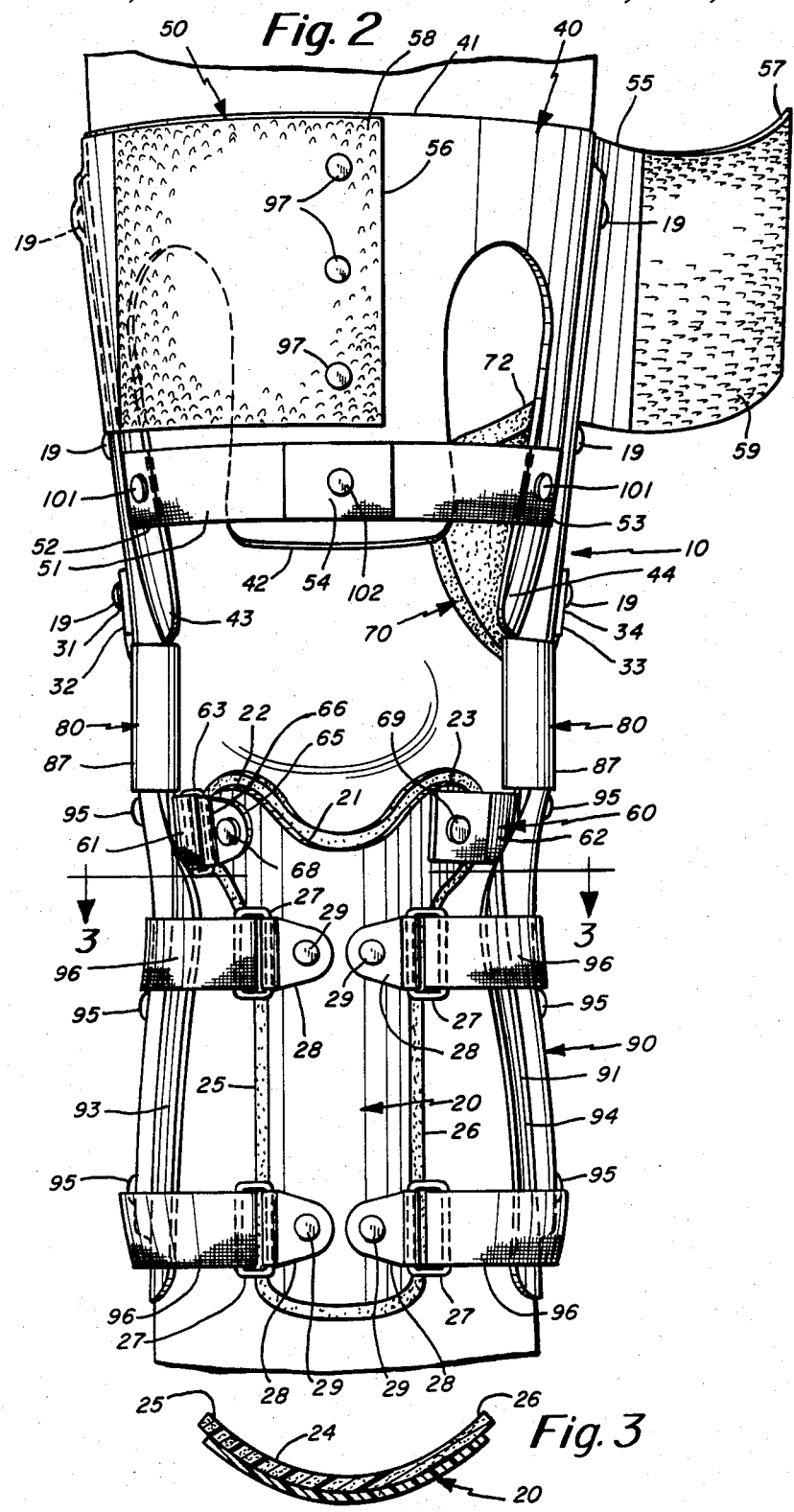

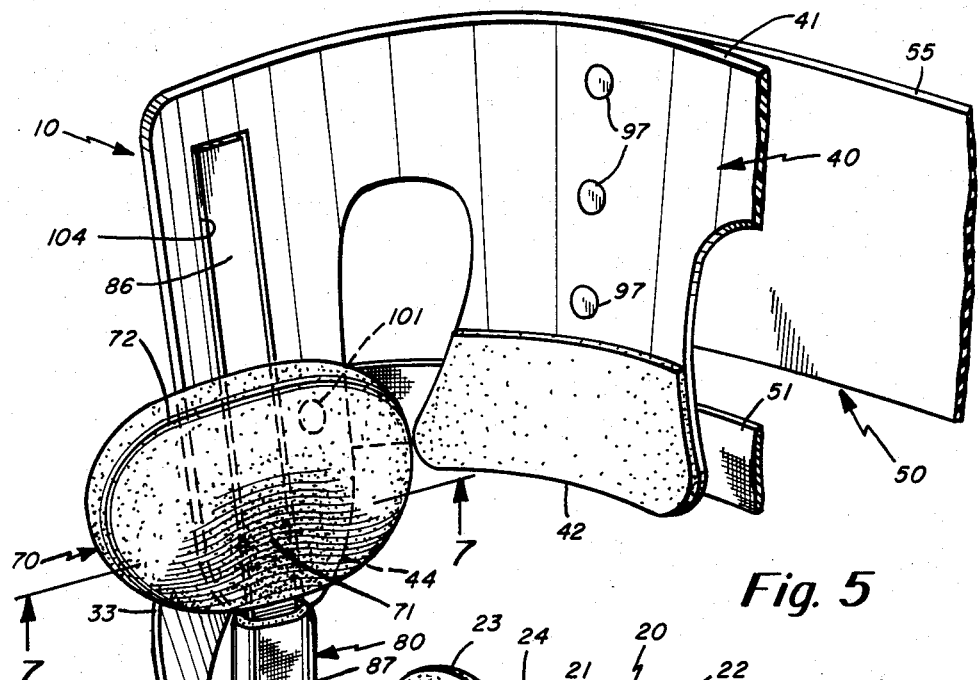
*Fig. 5*
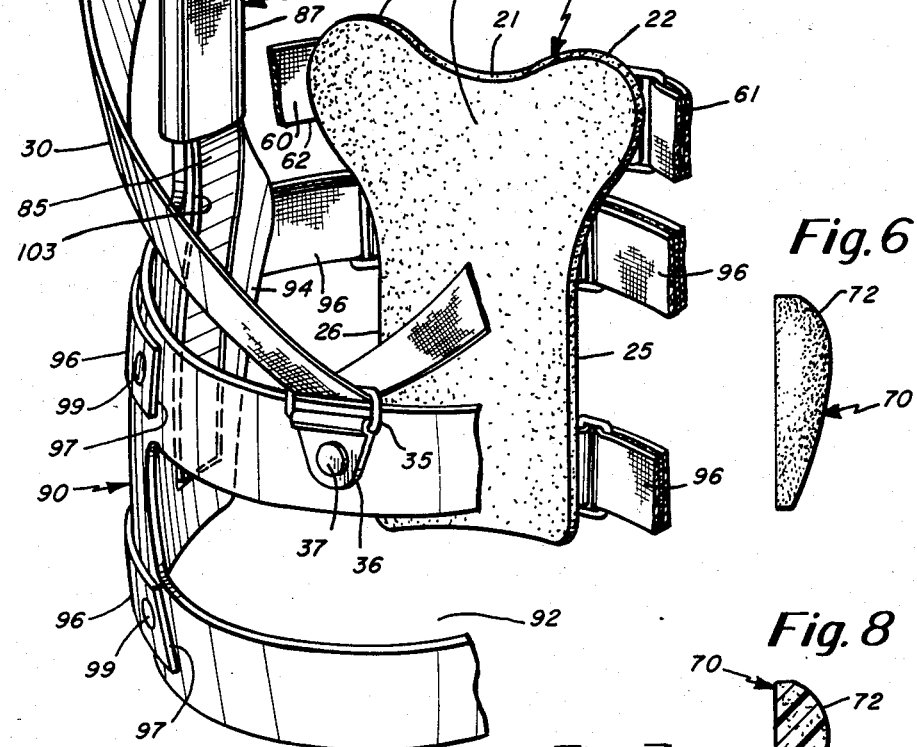
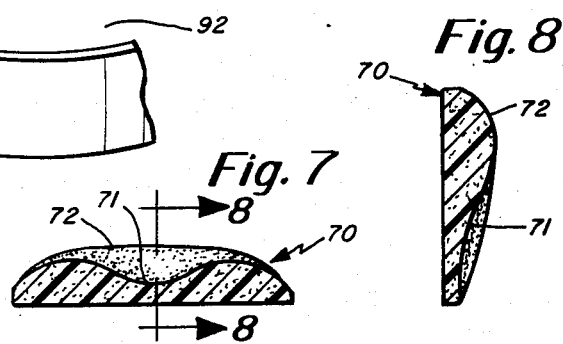
*Fig. 6*
*Fig. 8*
*Fig. 7*

KNEE BRACE FOR CONTROL OF LIGAMENT INSTABILITY

BACKGROUND OF THE INVENTION

This invention relates to knee braces and more particularly comprises an improved knee brace for controlling ligament instability in all planes.

When the ligaments surrounding the knee have been traumatized by injury or by surgery, a supporting brace is used to provide stability while allowing movement of the knee. The brace should provide stability against forces applied in the medial and lateral side planes and in the anterior and posterior planes. Further, the brace should provide rotational stability so as to prevent excessive rotation of the tibia in relation to the femur. The brace should also inhibit pivot shift (forward displacement of the tibia) by preventing the knee from achieving a full extension.

A known knee brace for controlling ligament instability includes a shin plate and a thigh plate connected in hinged relationship. The shin plate has a circular interior surface and is held on the shin by a wide calf band extending around the back of the leg at mid-calf. A pair of straps which criss-cross behind the back of the knee extend between opposing flanges on the top corners of the shin plate and points on the opposing sides of the thigh plate. An extension check strap, attached at opposing ends to opposing sides of the thigh plate, is looped around the calf band.

The known knee brace has numerous disadvantages. Principally, it fails to fully control ligament instability because it is not securely fastened to the leg. Further, the brace is uncomfortable and restrictive in that the cross straps behind the knee cause excessive chafing and their bulkiness behind the knee interferes with movement of the leg. The looping of the extension check strap around the calf band causes further abrasion and bulkiness behind the calf. The interior of the shin plate tends to press on the crest of the tibia bone and cause excessive abrasion.

It is an object of the invention to provide a knee brace which fully controls ligament instability while allowing natural action of the knee and which is both comfortable to wear and capable of being securely fastened to the leg.

SUMMARY OF THE INVENTION

The knee brace of the present invention includes a shin plate, a thigh plate, means for positioning the shin plate and thigh plate on the leg, means for connecting the shin plate and thigh plate in hinged relationship, and a popliteal strap. The shin plate has a top arcuate edge positionable below the front tibia tubrical and a pair of flanges extending from opposing corners of its top edge positionable over the side tibia tubricals on opposing sides of the tibia head. A tensioned popliteal strap attached at opposing ends to opposing flanges is positionable in a substantially horizontal plane around the back of the upper calf adjacent the knee to compress the flanges against the side tibia tubricals for increasing the rotational stability of the knee. The interior of the shin plate is parabolic-shaped to prevent chafing against the crest of the tibia and the elongated edges of the shin plate grasp opposing sides of the triangular-shaped tibia to increase the rotational stability of the knee. In a preferred embodiment, a condylar pad attached to the knee brace is positionable to engage the medial femoral epicondyl and condyl notch to prevent displacement of the knee brace on the leg. Further, an extension check strap connected at opposing ends to the brace on opposing sides of the thigh passes through a ring positioned on a calf band adjacent the back of the calf.

These and other objects and features of the present invention will be better understood and appreciated from the following detailed description of certain embodiments thereof, selected for purposes of illustration and shown in the accompanying drawings.

BRIEF DESCRIPTION OF THE DRAWINGS

FIG. 2 is a perspective and partial sectional view of the right knee brace viewed from the front;

FIG. 3 is a cross-sectional view of the shin plate taken along section lines 3—3 in FIG. 2;

FIG. 5 is a perspective and partial sectional view of the right knee brace viewed from the outer side of the leg;

FIG. 6 is a plan view of the condylar pad of the knee brace viewed from the side;

FIGS. 7 and 8 are cross-sectional views of the condylar pad taken along section lines 7—7 and 8—8 in FIGS. 5 and 7, respectively.

DETAILED DESCRIPTION OF THE INVENTION

Figure 1:
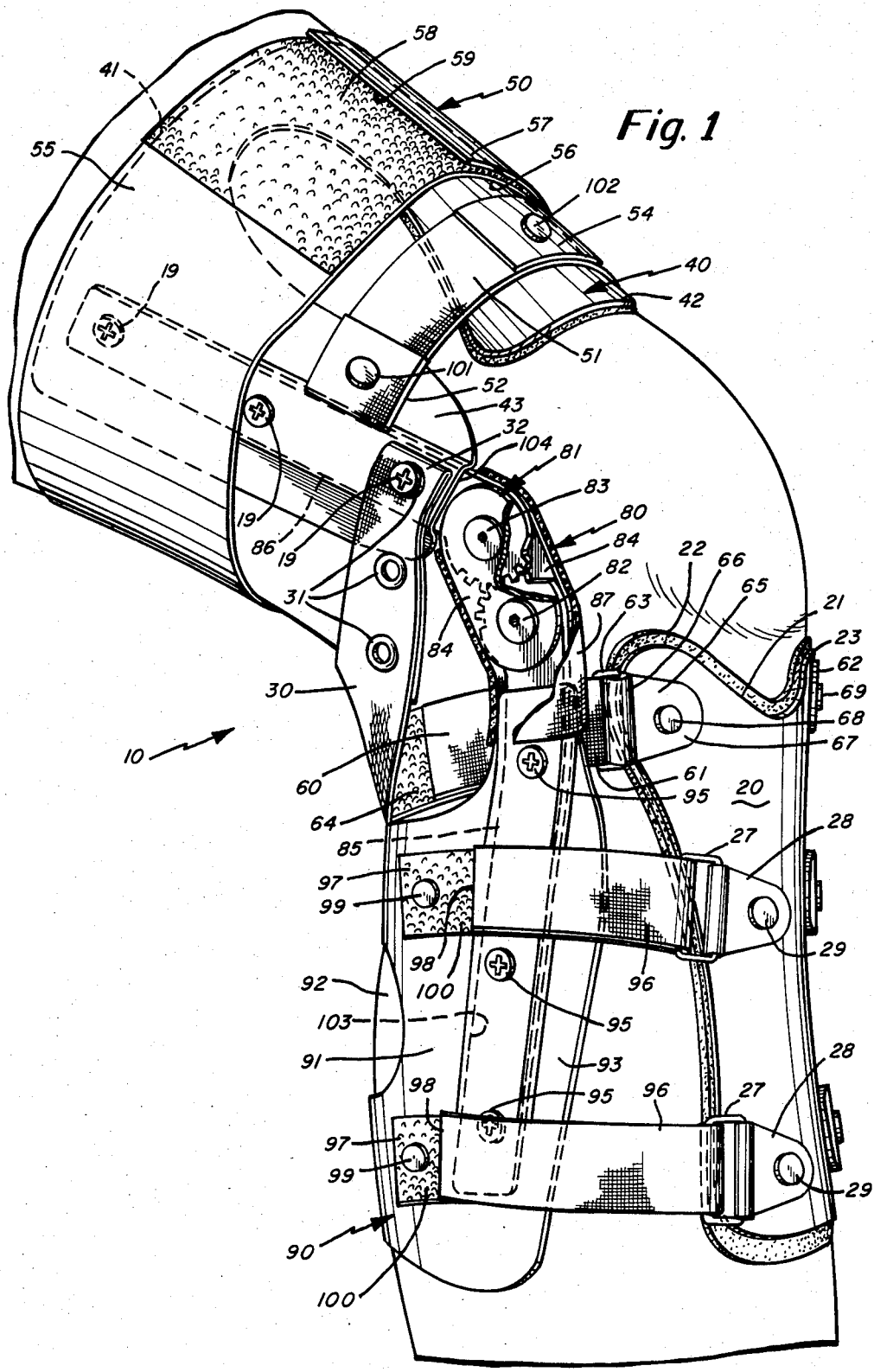
FIG. 1 is a perspective and partial sectional view of a right knee brace of this invention viewed from the outer side of the leg.

The knee brace 10 of the present invention, shown in FIG. 1, includes a shin plate 20, a thigh plate 40, means 90 and 50 for positioning the shin plate and thigh plate on the leg, respectively, means 80 for connecting the shin plate and thigh plate in hinged relationship, a popliteal strap 60, an extension check strap 30, and a condylar pad 70 (not visible in FIG. 1). The brace shown is designed for the right leg and a mirror image of the brace would be suitable for the left leg.

Figure 9:
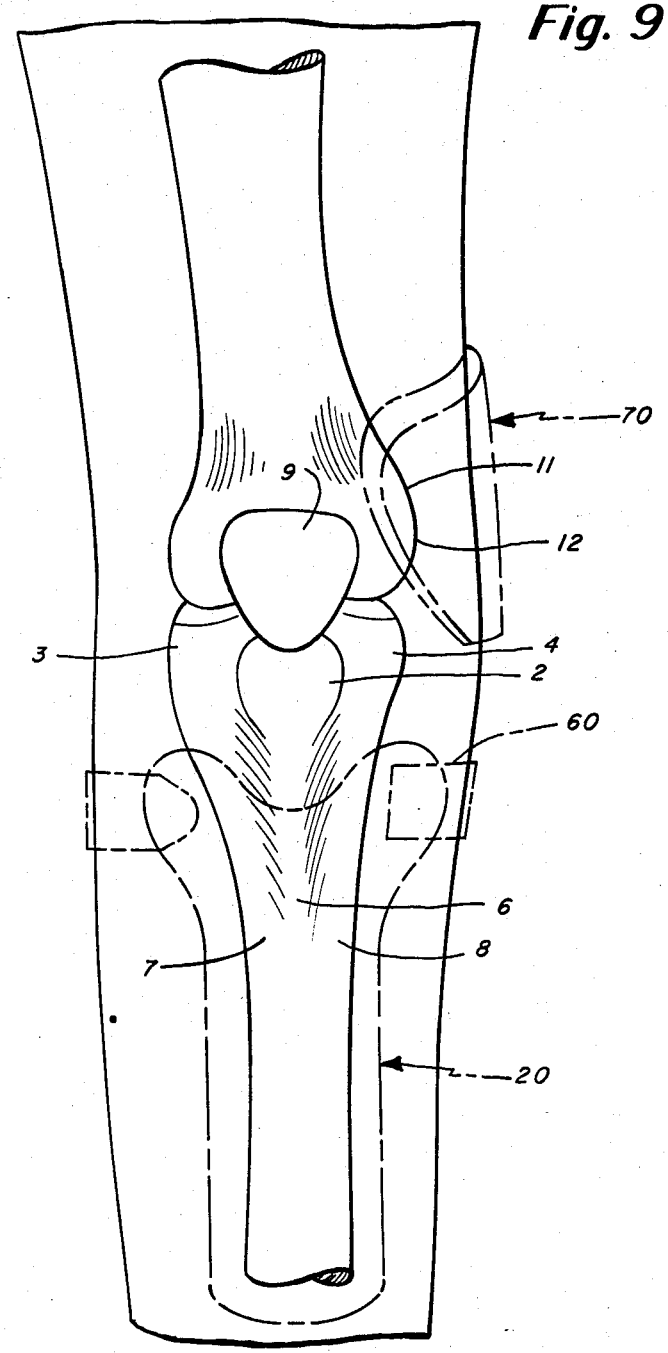
FIG. 9 is a diagrammatic view of the right knee and parts of the brace of the present invention in place on it and suggesting the manner in which the various components of the brace cooperate with the anatomy to perform their respective and combined functions.

The elongated shin plate 20, shown in FIGS. 1, 2, 5, and 9, is shaped to fit over the front of the leg and extend from the knee downwardly over the shin. The top arcuate edge 21 of the shin plate is positionable adjacent the bottom of the front tibia tubrical 2, as shown in FIG. 9. A pair of flanges 22 and 23 extend from opposing corners of the top edge of shin plate 20 and are positionable over the side tibia tubricals 3 and 4, respectively, on opposing sides of the tibia head.

A popliteal strap 60 is attached at opposing ends 61 and 62 to opposing flanges 22 and 23, respectively. Popliteal strap 60 is made of a flexible, elastic material and preferably is a one inch wide band of elasticized cotton. On the outer side of the leg, as shown in FIG. 1, end 61 is removably and adjustably attached to flange 22 by passing end 61 through a metal ring 63 and securing end 61 to a central portion of popliteal strap 60 by a Velcro-type attachment means 64. A leather or plastic tab 65 is attached at one end to ring 63 by loop 66 and is attached on its opposing end 67 to flange 22 by metal rivet 68. On the inner side of the leg, end 62 of popliteal strap 60 is permanently attached to flange 23 by a rivet 69 (see FIG. 2).

Figure 4:
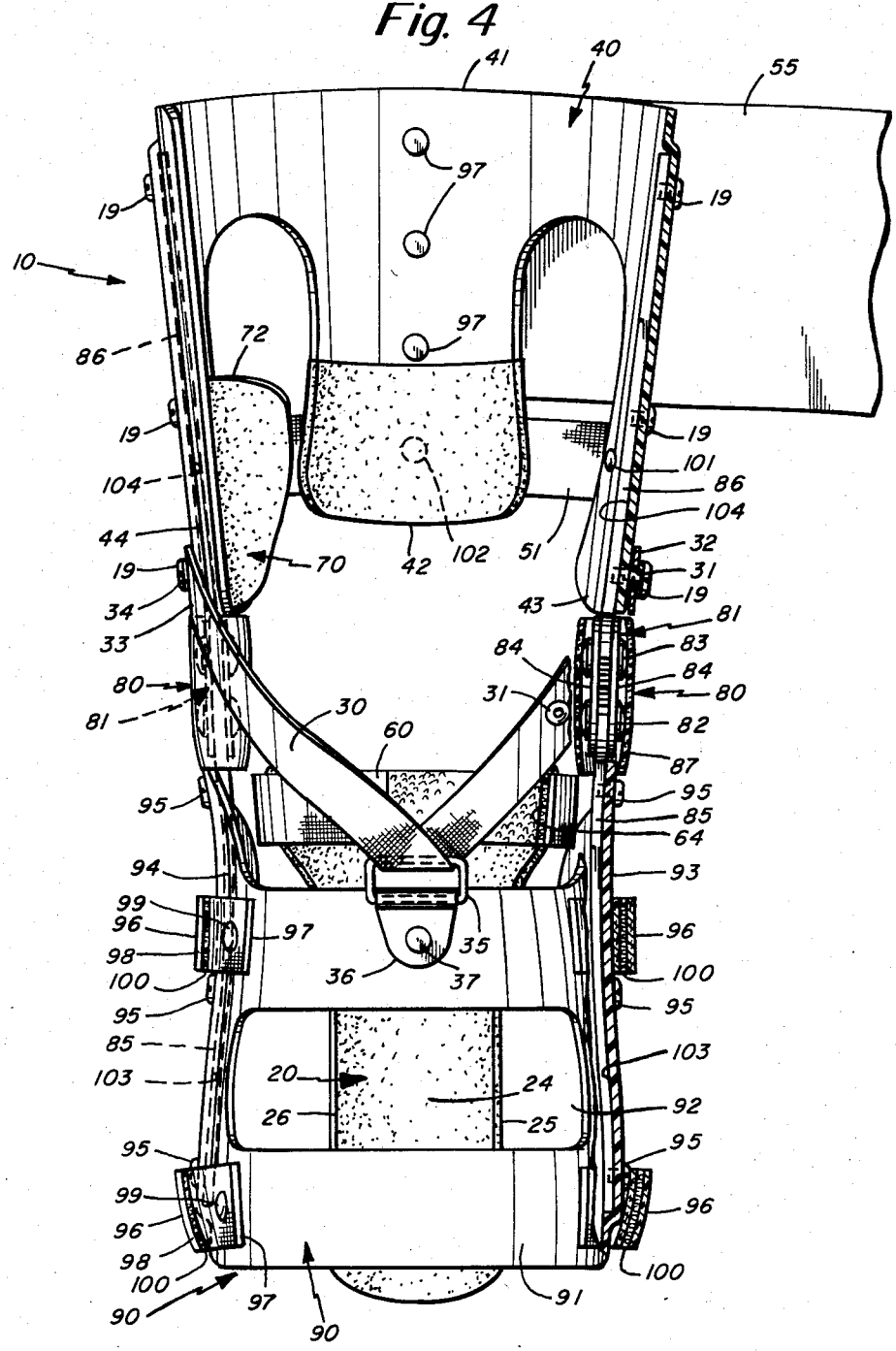
FIG. 4 is a perspective and partial sectional view of the right knee brace viewed from the back.

Popliteal strap 60 extends in a substantially horizontal plane around the back of the upper calf adjacent the knee (see FIG. 4) and is in tension in order to compress flanges 22 and 23 against side tibia tubricals 3 and 4 on opposing sides of the tibia head (see FIG. 9). By causing shin plate 20 to hug the tibia plateau laterally, and because shin plate 20 is aligned with thigh plate 40 as hereinafter described, popliteal strap 60 prohibits excessive rotation or misalignment of the tibia with respect to the femur. The knee can withstand additional force applied either anterior-medial or anterior-lateral.

Shin plate 20 is shown in cross-section in FIG. 3. The interior 24 of shin plate 20 is substantially parabolic-shaped rather than semi-circular for more secure attachment to the tibia and to prevent chafing against the tibia. The front of the tibia (see FIG. 9) is substantially triangular-shaped, comprising a longitudinally-extending crest or linea aspera 6 at the apex and in pair of longitudinally-extending surfaces 7 and 8 disposed on either side of crest 6. The more deeply concave interior of shin plate 20 prevents chafing against crest 6. The longitudinally-extending edges 25 and 26 of shin plate 20 grasp opposing sides 7 and 8 of the tibia for more secure attachment to the tibia to prevent the tibia from rotating separately from the femur and thus increase the rotational stability of the knee.

The exterior of shin plate 20 is made of an impact-resistant material which has sufficient flexibility to conform to the shape of the shin. Suitable materials include plastics such as polyethylene, polypropylene, and preferably a copolymer of the two such as that sold by General Tire & Rubber Co., New York, N.Y. The interior 24 of shin plate 20 is lined with a softer, less abrasive material such as the polyethylene foam known as "pelite".

Shin plate 20 is secured to the leg by shin plate positioning means 90. Means 90 includes a wide calf band 91 comprising a molded piece of flexible material which is wrapped around the back of the leg at the middle of the calf. Calf band 91 has an aperture 92 at the back of the calf and longitudinally extending side portions 93 and 94 on opposing sides of the leg. Calf band 91 is adjustably and removably attached to shin plate 20 by a pair of straps 96 on each side of the leg. Each of straps 96 is connected at one end 97 to calf band 91 by a rivet 99. The opposing end 98 of strap 96 is looped through a metal ring 27 and removably and adjustably attached to a central portion of strap 96 by Velcro-type attachment means 100. Each ring 27 is connected by tab 28 and rivet 29 to shin plate 20, similarly to tab 65 and rivet 68.

Thigh plate 40, shown in FIGS. 1, 2, 4, and 5, includes an upper portion 41, and integral therewith and extending downwardly therefrom, a suprapatellar flange 42 on the front of the thigh and two side projections 43 and 44 on opposing sides of the leg. Suprapatellar flange 42 has a lower edge positionable adjacent the top of the patella 9 to prevent knee brace 10 from sliding down on the leg. The interior of suprapatellar flange 42 is padded for comfort. Thigh plate 40 preferably consists of the same impact-resistant and flexible exterior and softer interior as shin plate 20.

Thigh plate 40 is secured to the leg by thigh plate positioning means 50. Means 50 includes a thigh strap 55 and a suprapatellar band 51.

Thigh strap 55 is an elastic band, approximately 4 inches wide, having opposing ends 56 and 57. End 56 is attached to thigh plate 40 by rivets 97. Thigh strap 55 is wrapped around the middle of the thigh over thigh plate 40 and end 57 is adjustably and removably secured by Velcro-type attachment means 58 and 59. The top edge of thigh strap 55 is preferably aligned with the top edge of thigh plate 40, and preferably lies approximately eight inches above the knee to provide leverage for restraining the ligaments of the knee.

Suprapatellar band 51 is an approximately one inch wide band of elastic material such as elasticized cotton. Band 51 is attached at its opposing ends 52 and 53 to opposing side projections 43 and 44 by rivets 101, and band 51 is attached at a central point 54 to suprapatellar flange 42 by rivet 102. Suprapatellar band 51 is in tension for securely holding the suprapatellar flange 42 against the leg above the knee and preventing the brace 10 from sliding down the leg.

On each side of the knee are means 80 for connecting shin plate 20 and thigh plate 40 in hinged relationship. As shown in FIG. 1, means 80 includes hinge 81 having multiple pivot points 82 and 83 and shafts 85 and 86 extending respectively below and above hinge 81. Pivot points 82 and 83 are joined by connecting means 84. Shaft 85 is connected to hinge 81 at pivot point 82 and extends downwardly therefrom to be attached at three vertically spaced points to side portion 93 of calf band 91 by screws 95. Shaft 85 is preferably disposed in a groove 103 on the interior surface of side portion 93. Shaft 86 is attached to hinge 81 at pivot point 83 and extends upwardly therefrom to be disposed in a groove 104 and attached at three vertically spaced points to side projection 43 of thigh plate 40 by screws 19. The shafts 85 and 86 maintain the vertical alignment of the femur and tibia and prevent excessive rotation of one with respect to the other. Shafts 85 and 86 are preferably each eight inches long in order to obtain substantial leverage.

Hinge 81 on each side of the knee includes a plurality of pivot points 82 and 83 to allow a full and natural bending of the knee. Natural minor displacements of the tibia in relation to the femur cause the knee to bend in various planes. These are accommodated by the multiple pivot points 82 and 83.

Each of hinges 81 is preferably encased by a sleeve 87 made of rubberized tubing or DACRON (registered trademark of E. I. duPont de Nemours & Co. Inc., Wilmington, Del.) to keep the hinge clean. Further, sleeve 87 prevents hinge 81 from chafing against the knee and injuring either the opposing leg or other articles which it accidentally contacts.

In a preferred embodiment, knee brace 10 includes an extension check strap 30 to prevent a complete unbending of the knee and thus prevent pivot shift. Check strap 30 is made of a strong and rigid material, and preferably is an approximately 1 inch wide band of DACRON (registered trademark of E. I. duPont de Nemours & Co. Inc., Wilmington, Del.). As shown in FIG. 1, at one end 32 of check strap 30 there are a plurality of apertures 31 for adjustable attachment to the bottom screw 19 on outer side projection 43. Opposing end 33 of strap 30 has one aperture 34 connected to inner side projection 44 by bottom screw 19 (FIG. 5). A central portion of check strap 30 passes through a metal ring 35, such as a D-ring, which ring is attached by tab 36 and rivet 37 to the upper portion of calf band 91 (see FIG. 4). Check strap 30 is thus adjustable and will not cause chafing behind the calf.

In a further preferred embodiment, a condylar pad 70 is disposed on the inner side of the leg above the knee to anchor knee brace 10 in place on the leg and prevent it from rotating (see FIGS. 2, 4, 5, and 9). Condylar pad 70 is essentially oval in shape with its long axis arranged horizontally. On one end condylar pad 70 is attached to inner side projection 44 and pad 70 extends forwardly from side projection 44 to engage the medial femoral epicondyl 12 and condyl notch 11 (see FIG. 9). A shallow cavity 71 and an enlarged ridge 72 are formed on the interior surface of condylar pad 70 as shown in FIGS. 6–8. Enlarged ridge 72 engages the condyl notch 11 while shallow cavity 71 actually fits over the epicondyl 12. The contours of condylar pad 70 and its location resist the tendency of the brace 10 to rotate outwardly about its vertical axis and slip downwardly on the leg. Condylar pad 70 is made of a rather stiff but yieldable plastic material such as a firm polyethylene foam. Condylar pad 70 may be cemented within a groove on the interior of the inner side projection 44.

The manner in which certain components of the knee brace 10 cooperate with the anatomy to perform their respective and combined functions is illustrated in FIG. 9. Popliteal strap 60 compresses the flanges 22 and 23 against opposing side tibia tubricals 3 and 4, thus preventing the tibia from excessive rotation or axial displacement with respect to the femur. The edges 25 and 26 of shin plate 20 grasp opposing sides 7 and 8 of the triangular-shaped tibia to further prevent displacement of the tibia with respect to the femur. The condylar pad 70 engages the medial femoral epicondyl 12 and condyl notch 11 for preventing rotation of the brace on the leg.

The knee brace of this invention is made according to known procedures involving the preparation of a plaster cast, vacuum molding of the thigh plate, shin plate, and calf band, shaping of the molded pieces for a precise fit, and attachment of the necessary hardware.

Having described this invention in detail, those skilled in the art will appreciate that numerous modifications may be made thereof without departing from the spirit of this invention. Therefore, it is not intended that the scope of the invention be limited to the specific embodiments illustrated and described. Rather, it is intended that the scope of the invention be determined by the appended claims and their equivalents.

What is claimed is:

1. An improved knee brace of the type having an elongated shin plate shaped to fit over the front of the leg and extend from the knee downwardly over the shin, a thigh plate shaped to fit over the front of the leg and extend from the knee upwardly over the thigh, means for positioning said shin plate and said thigh plate on the leg, and means for maintaining said shin plate and thigh plate in vertical alignment and connecting said shin plate and said thigh plate in hinged relationship to allow the knee to bend when said knee brace is positioned on the leg, wherein the improvement comprises:

said shin plate having a top arcuate edge positionable below the front tibia tubrical and having a pair of flanges extending from opposing corners of said top edge positionable over the side tibia tubricals on opposing sides of the tibia head;

a tensioned popliteal strap attached at opposing ends to said opposing flanges and positionable in a substantially horizontal plane around the back of the upper calf adjacent the knee to compress each of said flanges against the side tibia tubricals on opposing sides of the tibia head for increasing the rotational stability of the knee.

2. The knee brace of claim 1 wherein said shin plate has a parabolic-shaped interior to prevent chafing against the tibia crest and a pair of elongated edges positionable to grasp opposing sides of the triangular-shaped tibia for increasing the rotational stability of the knee.

3. The knee brace of claim 2 wherein said shin plate is made of an impact-resistant copolymer of polyethylene and polypropylene.

4. The knee brace of claim 3 wherein said popliteal strap is an approximately one inch wide band of elasticized cotton.

5. An improved knee brace of the type having an elongated shin plate shaped to fit over the front of the leg and extend from the knee downwardly over the shin, a thigh plate shaped to fit over the front of the leg and extend from the knee upwardly over the thigh, means for positioning said shin plate and said thigh plate on the leg, and means for maintaining said shin plate and thigh plate in vertical alignment and connecting said shin plate and said thigh plate in hinged relationship to allow the knee to bend when said knee brace is positioned on the leg, wherein the improvement comprises:

said shin plate having a top arcuate edge positionable below the front tibia tubrical and having a pair of flanges extending from opposing corners of said top edge positionable over the side tibia tubricals on opposing sides of the tibia head;

a tensioned popliteal strap attached at opposing ends to said opposing flanges and positionable in a substantially horizontal plane around the back of the upper calf adjacent the knee to compress each of said flanges against the side tibia tubricals on opposing sides of the tibia head for increasing the rotational stability of the knee;

a ring positioned on said shin plate positioning means adjacent the back of the calf; and an extension check strap connected at opposing ends to a pair of spaced points on said knee brace on opposing sides of the thigh and passing through said ring for preventing a complete unbending of the knee.

6. The knee brace of claim 1 further comprising:

a condylar pad attached to said knee brace and positionable to engage the medial femoral epicondyl and condyl notch for preventing displacement of said knee brace on the leg.

7. The knee brace of claim 1 wherein said vertical alignment and hinged means comprises on each side of the leg a multiple pivot hinge having shafts extending above and below the knee connected to said thigh plate and shin plate positioning means respectively and a sleeve disposed over said hinge for keeping the hinge clean and preventing the hinge from inflicting injury.

8. An improved knee brace of the type having an elongated shin plate shaped to fit over the front of the leg and extend from the knee downwardly over the shin, a thigh plate shaped to fit over the front of the leg and extend from the knee upwardly over the thigh, means for positioning said shin plate and said thigh plate on the leg, and means for maintaining said shin plate and thigh plate in vertical alignment and connecting said shin plate and said thigh plate in hinged relationship to allow the knee to bend when said knee brace is positioned on the leg, wherein the improvement comprises:

said shin plate having a top arcuate edge positionable below the front tibia tubrical and having a pair of flanges extending from opposing corners of said top edge positionable over the side tibia tubricals on opposing sides of the tibia head;

a tensioned popliteal strap attached at opposing ends to said opposing flanges and positionable in a substantially horizontal plane around the back of the upper calf adjacent the knee to compress said flanges against the side tibia tubricals on opposing sides of the tibia head for increasing the rotational stability of the knee;

said shin plate having a parabolic-shaped interior to prevent chafing against the tibia crest and a pair of elongated edges positionable to grasp opposing sides of the triangular-shaped tibia for increasing the rotational stability of the knee;

a ring positioned on said shin plate positioning means adjacent the back of the calf;

an extension check strap connected at opposing ends to a pair of spaced points on said knee brace on opposing sides of the thigh and passing through said ring for preventing a complete unbending of the knee; and a condylar pad attached to said knee brace and positionable to engage the medial femoral epicondyl and condyl notch for preventing displacement of said knee brace on the leg.

9. An improved knee brace of the type having an elongated shin plate shaped to fit over the front of the leg and extend from the knee downwardly over the shin, a thigh plate shaped to fit over the front of the leg and extend from the knee upwardly over the thigh, means for positioning said shin plate and said thigh plate on the leg, and means for maintaining said shin plate and thigh plate in vertical alignment and connecting said shin plate and said thigh plate in hinged relationship to allow the knee to bend when said knee brace is positioned on the leg, wherein the improvement comprises:

a ring positioned on said shin plate positioning means adjacent the back of the calf; and an extension check strap connected at opposing ends to a pair of spaced points on said knee brace on opposing sides of the thigh and passing through said ring for preventing a complete unbending of the knee.

* * * * *